United States Patent [19]
Viegas et al.

[11] Patent Number: 5,941,877
[45] Date of Patent: Aug. 24, 1999

[54] HAND EXTERNAL FIXATION AND JOINT MOBILIZATION AND DISTRACTION DEVICE

[75] Inventors: Steven F. Viegas; William L. Buford, Jr., both of Galveston, Tex.

[73] Assignee: The Board of Regents of the University of Texas System, Austin, Tex.

[21] Appl. No.: 09/006,878

[22] Filed: Jan. 14, 1998

[51] Int. Cl.[6] ................................................. A61B 17/60
[52] U.S. Cl. ............................................. 606/55; 606/54
[58] Field of Search .................................. 606/55, 54, 56, 606/57, 58, 59

[56] References Cited

U.S. PATENT DOCUMENTS

| | | |
|---|---|---|
| 4,628,919 | 12/1986 | Clyburn . |
| 5,122,140 | 6/1992 | Asche et al. . |
| 5,397,322 | 3/1995 | Campopiano . |
| 5,429,637 | 7/1995 | Hardy . |
| 5,437,667 | 8/1995 | Papierski et al. . |
| 5,624,440 | 4/1997 | Huebner . |
| 5,709,681 | 1/1998 | Pennig ........................................ 606/54 |
| 5,743,898 | 4/1998 | Bailey et al. .............................. 606/54 |

*Primary Examiner*—Guy V. Tucker
*Attorney, Agent, or Firm*—Rosenblatt & Redano, P.C.

[57] ABSTRACT

This invention is directed toward a hand fracture, burn and contraction treatment device that is capable of imparting the desired amount of long term force and moment to the interphalangeal and metacarpalphalangeal joints so as to effectively combat deformity due to burn scar or trauma, to prevent and/or correct contractures, and to reduce and immobilize fractures. The invention comprises two axial members slidably mounted within respective housings and joined by a spherical joint (with a slot to provide a selectable axis of increased range of motion). The invention permits movement of one axial member with respect to the other axial member in up to five degrees of freedom. The invention further provides for the adjustable mobilization of each axial member.

20 Claims, 3 Drawing Sheets

HAND EXTERNAL FIXATION AND JOINT MOBILIZATION AND DISTRACTION DEVICE

BACKGROUND OF THE INVENTION

1. Field of the Invention

This invention is directed toward a hand fracture, burn and contraction treatment device that is capable of imparting the desired amount of long term force and moment to the interphalangeal and metacarpalphalangeal joints so as to effectively combat deformity due to burn scar or trauma, to prevent and/or correct contractures, and to reduce and immobilize fractures. The invention comprises two axial members slidably mounted within respective housings and joined by a spherical joint (with a slot to provide a selectable axis of increased range of motion). The invention permits movement of one axial member with respect to the other axial member in up to five degrees of freedom. The invention further provides for the adjustable mobilization of each axial member.

2. Description of the Prior Art

The prevention and correction of deformity following burns is a difficult challenge for those in the art of burn contracture therapy. After a severe burn the burn scar contracts. Where the patient receives severe burns to the hand, the resulting contraction can result in the fingers being pulled back such that the normal range of movement of the fingers is severely diminished or lost completely. A similar loss of movement can result in the wrist where the wrist sustains severe burns.

Prior art fixation devices for use with the hand have been directed toward static fixation about the wrist. Such devices are disclosed in U.S. Pat. Nos. 4,628,919 to Clyburn, and 5,122,140 to Asche et al. Wrist fixators are too large and heavy for use in finger fixation. Additionally, the motion capability that is sufficient for a wrist fixator is different from that needed for a finger fixator.

Prior art fixation devices are directed toward placing the joint in a fixed axis or selected position. The adjustability of such devices is with respect to the position of fixation. Burn contracture patients are also in need of physical therapy which involves cam-like motion of the limbs about the joint where fixation is applied. Prior art devices do not provide for the adjustable complex anatomic movement of the fixation elements to enable the patient to engage in repetitive flexion—extension and ulnarradial deviation.

SUMMARY OF THE INVENTION

The present invention is directed toward a hand fixation and complex anatomic motion device that is sufficiently small and light to be installed on a human finger for use about the interphalangeal and metacarpalphalangeal joints. The present invention may also be used with other bones and joints. The invention permits selective movement in up to five degrees of freedom.

The invention comprises a first housing, and a first axial member slidably housed within the first housing and comprising a distal end and a proximal end. The proximal end of the first axial member extends beyond the first housing.

The invention further comprises a spherical joint housing comprising an outside and an inside. The spherical joint housing is attached to the proximal end of the first axial member.

The invention further comprises a first adjustable motion restraining device attached to the first housing and capable of adjustably engaging the first axial member so as to guide or selectively restrain the movement of said axial member.

The invention further comprises a second housing, and a second axial member slidably housed within the second housing and comprising a distal end and a proximal end. The proximal end of the second axial member extends beyond the second housing.

The invention further comprises a second adjustable motion restraining device attached to the second housing and capable of adjustably engaging the second axial member so as to guide or selectively restrain the movement of said axial member.

The invention further comprises a spherical joint attached to the proximal end of the second axial member. The spherical joint is rotatably connected to the inside of the spherical joint housing. The invention further comprises an adjustable rotation motion device attached to the spherical joint or to the spherical joint housing. The adjustable rotation motion device is capable of adjustably guiding the movement of the spherical joint in one or more degrees of freedom. The adjustable rotation motion device comprises a slot which provides for a selectable axis with increased range of motion.

The five degrees of freedom permitted by the present invention include two axial degrees of freedom, backwards and forwards, for the first and second axial members, and three rotational degrees of freedom for the spherical joint with respect to the spherical joint housing. These five degrees of freedom are depicted in FIG. 6.

The first two rotational degrees of freedom are rotation of the spherical joint in two separate two dimensional planes positioned at right angles to each other. These degrees of freedom are analogous to pitch and yaw in the aviation arts. The angles of rotation in each two dimensional plane are depicted as $A_{xy}$ and $B_{zx}$ in FIG. 6.

The third rotational degree of freedom is rotation of the second axial member with respect to the first axial member at the spherical joint, such that the second axial member rotates about its own longitudinal axis in three dimensional space, as shown in FIG. 6. This degree of freedom is analogous to roll in the aviation arts.

DESCRIPTION OF THE PREFERRED EMBODIMENTS

Figure 1:
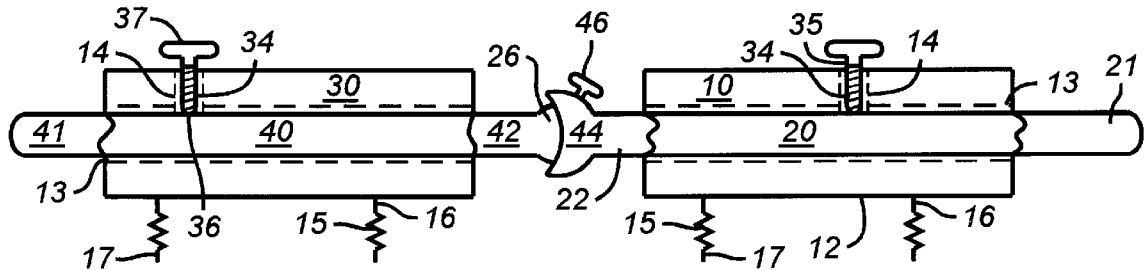
FIG. 1 is a side view of one embodiment of the present invention.
Figure 2:
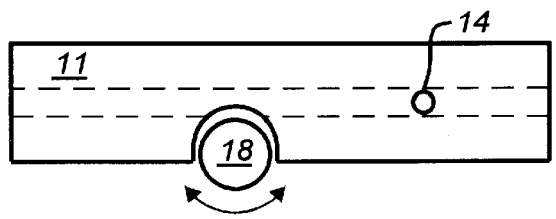
FIG. 2 is a top view of one embodiment of the present invention.

In a preferred embodiment, as shown in FIG. 1, the invention comprises a first housing 10 comprising a top surface 11, a bottom surface 12, and a central axial channel 13. A first axial member 20 is slidably housed within the central axial channel of the first housing. The first axial member comprises a distal end 21 and a proximal end 22. The proximal end extends beyond the first housing. In a preferred embodiment, a first position adjusting device 18, as shown in FIG. 2, is mounted on the first housing so as to rotatably engage the first axial member.

A first adjustable motion restraining device 34 is attached to the first axial member. This device is capable of guiding or selectively restraining axial movement of the first axial member as shown in FIG. 1.

Figure 3:
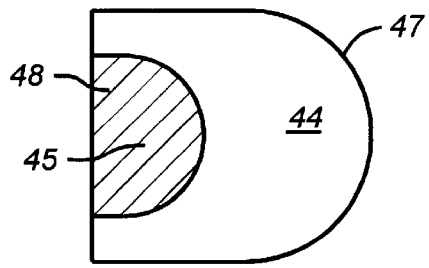
FIG. 3 is a top view of one embodiment of the spherical housing of the present invention.
Figure 5:
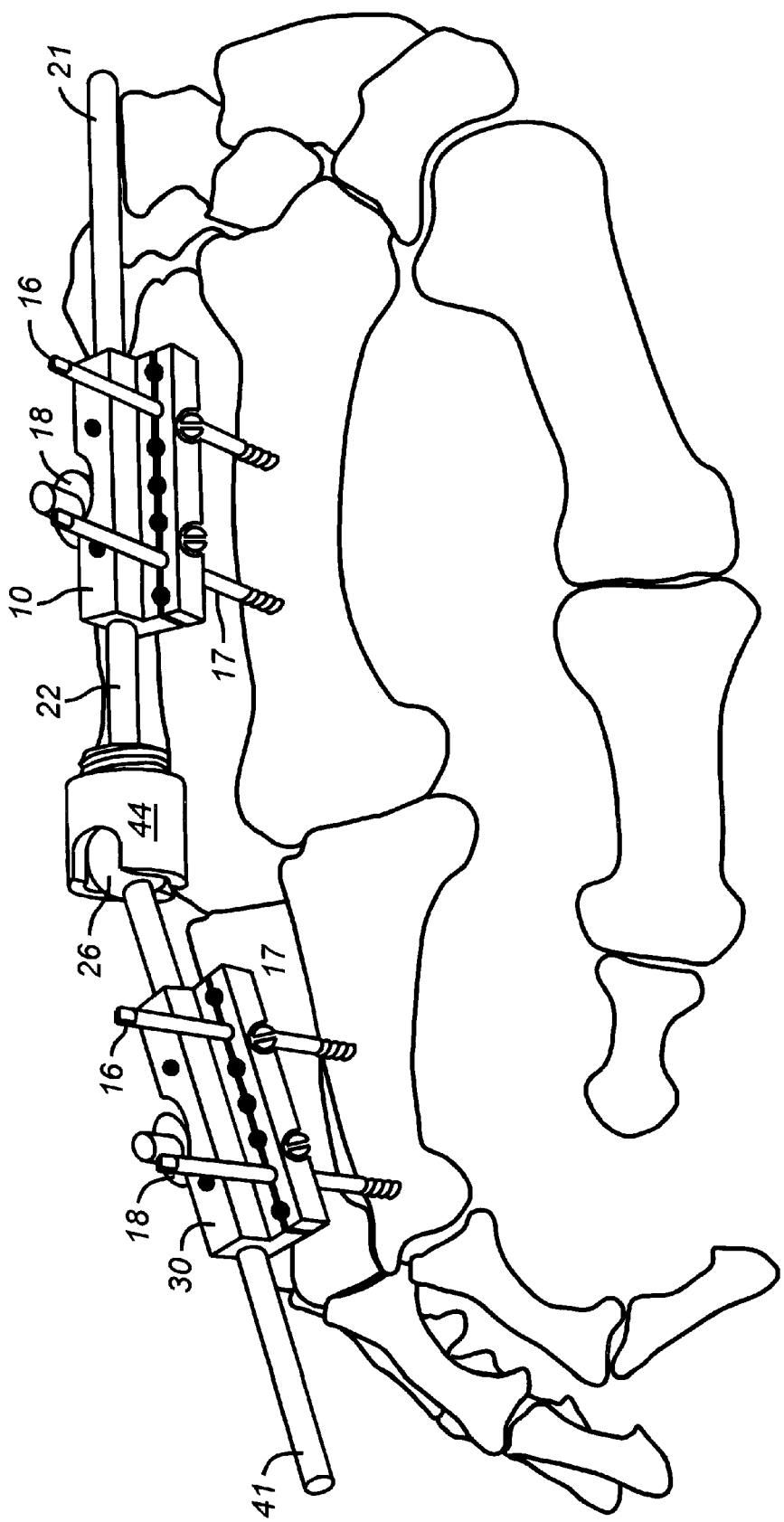
FIG. 5 is a side view of the present invention installed on the hand of a human patient.
Figure 6:
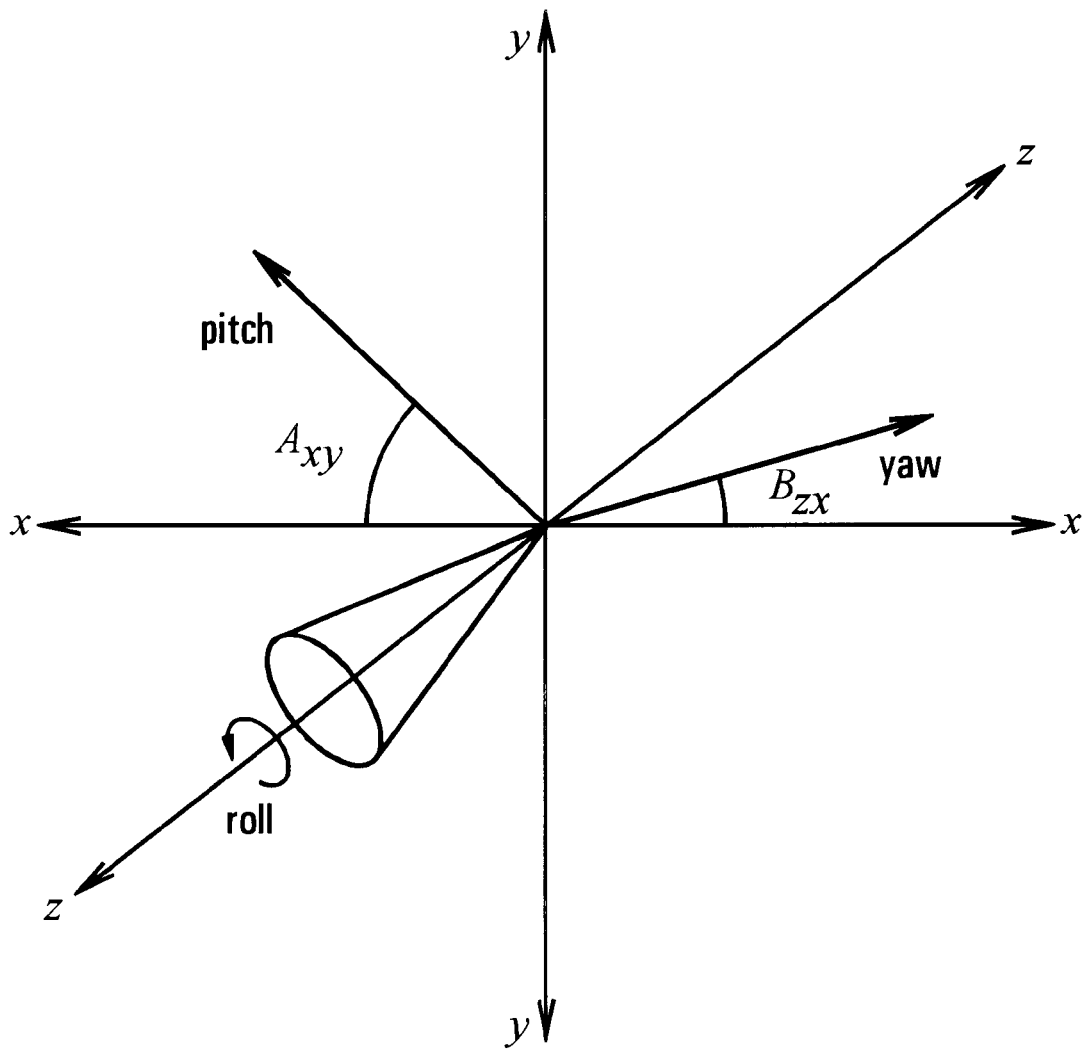
FIG. 6 is an isometric view illustrating the three rotational degrees of freedom available with the present invention.

A spherical joint housing 44 is attached to the proximal end of the first axial member. The spherical joint housing comprises an outside 47, an inside 48 and a recess 45, as shown in FIGS. 1, 3, and 5. In a preferred embodiment, the recess of the spherical joint housing is of sufficient size to allow the axial members to be positioned at a right angle with respect to each other. In a preferred embodiment, as shown in FIG. 1, the joint housing 44 is rigidly attached to the proximal end of the first axial member 22. This rigid attachment prohibits rotation of the joint housing with respect to the first axial member, as shown in FIG. 1.

The invention further comprises a second housing 30 comprising a top surface 11, a bottom surface 12, and a central axial channel 13. In a preferred embodiment, the top surfaces of the first and second housings comprise a threaded channel 14 positioned over the axial member slidably mounted in the housing. In this preferred embodiment, the first and second adjustable motion restraining devices are set screws threadably inserted into the first and second threaded channels, as shown in FIG. 1. Each of these set screws comprises an upper end 35 and a lower end 36, as shown in FIG. 1. The lower ends of the set screws are capable of engaging the axial member.

In another preferred embodiment, each of the set screws is attached to a head 37. In a preferred embodiment, the diameter of the head is greater than the diameter of the set screw to which it is attached.

In a preferred embodiment, a pair of mounting pins 15 are attached to the first and second housings, as shown in FIGS. 1 and 5. The mounting pins comprise an upper end 16 and a lower end 17. The mounting pins are attached at their upper ends to one of the housings. In a preferred embodiment the mounting pins are 1 millimeter fix pins. In a preferred embodiment, the lower ends of the mounting pins are threaded and are capable of penetrating the bone of a human finger.

A second axial member 40 is slidably housed within the central axial channel of the second housing, as shown in FIG. 1. The second axial member comprises a distal end 41 and a proximal end 42. The proximal end extends beyond the second housing. In one preferred embodiment, the first and second axial members are cylindrical. In another preferred embodiment, the first and second axial members are smooth.

In a preferred embodiment, a second position adjusting device 18 is mounted on the second housing so as to rotatably engage the second axial member, as shown in FIG. 5. Rotation of the first and second position adjusting devices is translated to axial movement of the corresponding axial member which engages the respective position adjusting device. In a preferred embodiment, the first and second position adjusting devices are cylindrical knobs rotatably mounted to the first or second housing such that the cylindrical surface of the knob rotatably engages the respective axial member, as shown in FIG. 2.

The invention further comprises a second adjustable motion restraining device 34 attached to the second axial member. In a preferred embodiment, the first and second adjustable motion restraining devices are set screws, as shown in FIG. 1.

A spherical joint 26 is attached to the proximal end of the second axial member. The spherical joint is rotatably connected to the inside of the spherical joint housing. An adjustable rotation motion device 46, as shown in FIG. 1, is coupled to the spherical joint or to the spherical joint housing. In one preferred embodiment, the rotation motion device is a set screw.

Figure 4:
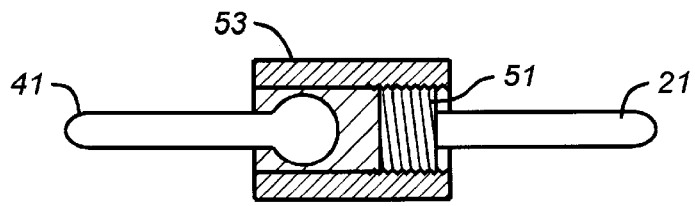
FIG. 4 is a side cross sectional view of another embodiment of the spherical joint and spherical joint housing of the present invention.

Another embodiment of the adjustable rotation motion device of the present invention is depicted in FIG. 4. In this embodiment, a braking member 51 is attached to the proximal end of the first axial member. A threaded sleeve 53 is coupled to the braking member and the spherical joint such that the rotation of the sleeve relative to the braking member can cause the braking member to be compressed against the spherical joint, thereby restraining the rotation of the spherical joint.

The device of the present invention is intended for installation in human hands (thumb/fingers). In a preferred embodiment, as shown in FIG. 5, the lengths of the first and second housings are less than the lengths of the finger segments to which they are attached.

The foregoing disclosure and description of the invention are illustrative and explanatory. Various changes in the size, shape, and materials, as well as in the details of the illustrative construction may be made without departing from the spirit of the invention.

What is claimed is:

1. A hand fracture, burn and contracture treatment device comprising:
   a. a first housing;
   b. a first axial member slidably housed within said first housing and comprising a distal end and a proximal end, said proximal end extending beyond said first housing;
   c. a first adjustable motion restraining device attached to said first housing and capable of adjustably engaging said first axial member so as to guide or restrain the movement of said first axial member;
   d. a spherical joint housing comprising an outside and an inside, said spherical joint housing attached to the proximal end of said first axial member;
   e. a second housing;
   f. a second axial member slidably housed within said second housing and comprising a distal end and a proximal end said proximal end extending beyond said second housing;
   g. a second adjustable motion restraining device attached to said second housing and capable of adjustably engaging said second axial member so as to guide or restrain the movement of said second axial member;
   h. a spherical joint attached to the proximal end of said second axial member, said spherical joint rotatably connected to the inside of said spherical joint housing; and
   i. an adjustable rotation motion device attached to said spherical joint or to said spherical joint housing and capable of adjustable restraining or preventing the movement of said spherical joint in one or more degrees of freedom.

2. The device of claim 1, wherein said first and second axial members are cylindrical.

3. The device of claim 2, further comprising a position adjusting device mounted on said first housing so as to engage the axial member in said first housing.

4. The device of claim 3, wherein said position adjusting device is a cylindrical knob rotatably mounted in said first housing such that it rotatably engages said first axial member.

5. The device of claim 1, wherein the outer surfaces of said second axial member is smooth.

6. The device of claim 1, wherein said second adjustable motion restraining device is a set screw.

7. The device of claim 1, wherein said rotation motion device is a set screw and wherein said joint housing is rigidly attached to the proximal end of said first axial member.

8. The device of claim 1, wherein said spherical joint housing comprises a recess of sufficient size to allow said axial members to be positioned at a right angle with respect to each other.

9. The device of claim 1, further comprising a pair of mounting legs comprising upper ends and lower ends, said mounting legs attached to at their upper ends to each of said housings.

10. The device of claim 9, wherein the lower ends of each of said mounting legs are threaded.

11. A hand fracture, burn and contracture treatment device comprising:
   a. a first housing comprising a top surface, a bottom surface and a central axial channel;
   b. a first axial member slidably housed within said central axial channel of said first housing and comprising a distal end and a proximal end, said proximal end extending beyond said first housing;
   c. a first position adjusting device mounted on said first housing so as to rotatably engage said first axial member;
   d. a first adjustable motion restraining device coupled to said first axial member;
   e. a spherical joint housing comprising an outside, an inside and a recess, said spherical joint housing attached to the proximal end of said first axial member;
   f. a second housing comprising a top surface, a bottom surface and a central axial channel;
   g. a second axial member slidably housed within said central axial channel of said second housing and comprising a distal end and a proximal end said proximal end extending beyond said second housing;
   h. a second adjustable motion restraining device coupled to said second axial member;
   i. a spherical joint attached to the proximal end of said second axial member, said spherical joint rotatably connected to the inside of said spherical joint housing; and
   j. an adjustable rotation motion device coupled to said spherical joint or to said spherical joint housing.

12. The device of claim 11, wherein said position adjusting device is a cylindrical knob rotatably mounted such that it rotatably engages said first axial member.

13. The device of claim 11, wherein said top surfaces of said second housing comprises a threaded channel positioned over said axial member.

14. The device of claim 13, wherein said second adjustable motion restraining device is a set screw threadably inserted into said threaded channel said set screw comprising a lower end and an upper end, said lower end being capable of engaging said second axial member.

15. The device of claim 14, further comprising a head attached to said upper end of each set screw, the diameter of said head being greater than the diameter of the set screw to which it is attached and wherein said joint housing is rigidly attached to the proximal end of said first axial.

16. The device of claim 11, wherein said recess is of sufficient size to allow said axial members to be positioned at a right angle with respect to each other.

17. The device of claim 11, further comprising a pair of mounting legs comprising upper ends and pointed lower ends capable of penetrating the bone of a human finger, said mounting legs attached to at their upper ends to the bottom surface of each of said housings.

18. The device of claim 11, wherein said rotation motion device comprises a braking member attached to the proximal end of said first axial member and a threaded sleeve encasing said braking member and said spherical joint such that the rotation of said sleeve relative to said braking member can cause said braking member to restrain the rotation of said spherical joint.

19. A hand fracture, burn and contracture treatment device comprising:
   a. a first housing comprising a top surface, a bottom surface, a central axial channel, and a threaded channel extending through said top surface;
   b. a first axial member slidably housed within said central axial channel of said first housing and comprising a distal end and a proximal end, said proximal end extending beyond said first housing;
   c. a set screw mounted in the threaded channel of said first housing so as to rotatably engage said first axial member;
   d. a first adjustable motion restraining device coupled to said first axial member;
   e. a spherical joint housing comprising an outside, an inside and a recess, said spherical joint housing rigidly attached to the proximal end of said first axial member;
   f. a second housing comprising a top surface, a bottom surface, a central axial channel, and a threaded channel extending through said top surface;
   g. a second axial member slidably housed within said central axial channel of said second housing and comprising a distal end and a proximal end said proximal end extending beyond said second housing;
   h. a set screw mounted in the threaded channel of said second housing so as to rotatable engage said first axial member;
   i. a second adjustable motion restraining device coupled to said second axial member;
   j. a spherical joint attached to the proximal end of said second axial member, said spherical joint rotatably mounted inside of said spherical joint housing; and
   k. an adjustable rotation motion device coupled to said spherical joint or to said spherical joint housing.

20. The device of claim 19 wherein the lengths of said first and second housing are less than the lengths of the finger segments to which they will be attached.

* * * * *